United States Patent [19]

Barton et al.

[11] 4,260,579

[45] Apr. 7, 1981

[54] DEVICE AND METHOD FOR SIMULATING BILIRUBIN IN URINE

[75] Inventors: Nancy K. Barton; Carmine M. Greene; Myron C. Rapkin, all of Elkhart, Ind.

[73] Assignee: Miles Laboratories, Inc., Elkhart, Ind.

[21] Appl. No.: 37,647

[22] Filed: May 10, 1979

[51] Int. Cl.$^3$ .................. G01N 33/52; G01N 33/62
[52] U.S. Cl. .................................. 422/56; 23/230 B; 23/905; 252/408
[58] Field of Search ............... 23/230 B, 905; 422/55, 422/56; 252/408

[56] References Cited

U.S. PATENT DOCUMENTS

| | | | |
|---|---|---|---|
| 3,477,818 | 11/1969 | Fried | 23/230 B |
| 3,511,607 | 5/1970 | Green | 23/230 B |
| 3,526,479 | 9/1970 | Ry et al. | 23/230 B |
| 3,652,222 | 3/1972 | Denney | 23/230 B |
| 3,850,576 | 11/1974 | Rittersdorf et al. | 252/408 X |
| 3,853,466 | 12/1974 | Rittersdorf et al. | 252/408 X |

*Primary Examiner*—Michael S. Marcus
*Attorney, Agent, or Firm*—Edward H. Gorman, Jr.

[57] ABSTRACT

A device and method are disclosed for preparing a bilirubin-containing control solution. The device comprises a carrier vehicle having incorporated with it unconjugated bilirubin and certain dyes. Upon contact with a predetermined quantity of water a control solution results, which will simulate a pathological specimen of conjugated bilirubin-containing solution, upon analysis.

23 Claims, No Drawings

DEVICE AND METHOD FOR SIMULATING BILIRUBIN IN URINE

BACKGROUND OF THE INVENTION

1. Field of the Invention

When a procedure is devised for determining the presence of a sample constituent—be the devised procedure gravimetric, volumetric, spectrophotometric or whatever mode—its efficacy in producing reliable results must somehow be assessed. Otherwise, the data developed is meaningless. Hence, devising an analytical procedure extends far beyond building a machine, formulating reagents or developing a technique. It also must of necessity include evaluating experimental error. There must be a way of predicting the dependability of the data produced by the procedure.

The easiest, most direct way to study parameters such as reproducibility, sensitivity, accuracy and need for calibration is to subject the procedure to a test sample wherein the analyte presence and/or concentration is known beforehand, i.e., a control solution. The data furnished by the procedure can then be compared with known data and any discrepancies properly noted.

The present invention concerns itself with the assessment of procedures for determining the presence and/or concentration of bilirubin in a liquid sample. Moreover, it relates to a device for preparing a bilirubin control solution for use in assessing the performance of various bilirubin determination procedures.

The chemistry and biology of the bile pigments are quite complicated; some of the steps in the metabolic pathways being still shrouded in mystery. Much of the older literature on the subject is now obsolete, and not of primary concern to the clinical chemist. Bilirubin, however, is one of the bile pigments occurring somewhat early in the metabolism of heme, and substantial analytical literature is available.

Bilirubin originates primarily from the breakdown of the heme moiety of hemoglobin in senescent erythrocytes by the reticulo-endothelial system. This occurs primarily in the spleen, liver and bone marrow.

Bilirubin which is formed from the breakdown of hemoglobin is transported in the plasma bound to a carrier such as albumin or, in small amounts, $\alpha$-globulins and other serum proteins. Anionic drugs, such as salicylates and sulfa, or other anions, such as free fatty acids, can compete for these binding sites and substantially reduce the bilirubin transport capacity of the plasma. It is hypothesized that bilirubin dissociates from its carrier protein in the liver cell membrane, and it is transported intracellularly by some act or process, either unbound or attached to high-affinity, specific acceptor systems.

Conjugation of bilirubin with glucuronic acid, and, to a lesser extent with sulfuric and possibly other acids, occurs in the liver. Conjugated bilirubin is excreted from the liver cell into the bile canaliculus. In the intestinal tract a small fraction of the conjugated bilirubin excreted in the bile is hydrolyzed and the unconjugated bilirubin reabsorbed. Consequently, practically all excreted bilirubin is in the conjugated form.

The diagnostic value of determining bilirubin in urine has long been recognized. Normal urinary bilirubin levels are less than about 0.05 milligrams per deciliter (mg%). Accordingly, elevated bilirubin levels in urine connote the possible existence of a pathological condition in a patient. For example, high bilirubin levels can result from biliary obstruction, and hemolytic and hepatic disease. It is generally recognized that the presence of bilirubin in urine at concentrations greater than the abovementioned 0.05 mg% indicates the desirability of performing more comprehensive diagnostic procedures determinative of the specific pathological condition causing the elevated urinary bilirubin concentration.

As stated supra, essentially all bilirubin appearing in pathological urines or other bodily excreta is in the glucuronate conjugated form. Many analytical systems exist in the art for determining this form of bilirubin.

2. Description of the Prior Art

Over 70 tests have been proposed for the qualitative determination of bilirubin in urine. In general, these can be grouped into four categories depending on the principle used: (a) observation of the color of the urine sample; (b) the titration of the urine sample with a dye (e.g. methylene blue) until the dye color dominates over the bilirubin color; (c) oxidation of bilirubin to characteristic colors; and (d) diazo-coupling. Moreover, there are commercially available dip-and-read reagent strips on the market, such as those available from the Ames Division of Miles Laboratories, Inc., known as BILI-LABSTIX®, ICTOSTIX®, MULTISTIX®, and N-MULTISTIX®, as well as ICTOTEST® reagent tablets, also available from Ames Division.

Bilirubin is conventionally determined in routine urinalysis based on its reaction with various diazonium compounds in an acidic medium to form a colored azobilirubin complex. While several test formats are reported in the literature, the most commonly used test format in the clinical laboratory is that generally referred to as a test strip. The diazonium compound is incorporated in a carrier capable of absorbing a predetermined amount of urine when dipped momentarily into a urine sample. Any resulting colorimetric response may be read in less than one minute. Such test strips as those Ames Division products exemplified above utilize these principles.

The preparation and use of a bilirubin test strip is described in detail in U.S. Pat. No. 3,585,001. While the test strips which have been described in the art provide very rapid and convenient means for detecting urinary bilirubin, it is generally known that the available test strips are not sufficiently sensitive to detect levels of bilirubin only slightly elevated from the normal level, i.e., between 0.2 and 0.4 milligram (mg) bilirubin per 100 milliliter (ml).

There have been a few reported attempts to increase the sensitivity of the reaction between diazonium compounds and urinary bilirubin; however, the test systems that have resulted have certain disadvantages. U.S. Pat. No. 3,880,588 describes a class of diazonium compounds designed to enhance the colorimetric response of the azobilirubin complex and to decrease interfering color reactions with urobilinogen, which is structurally and chemically very similar to bilirubin. The described diazonium compounds, unlike the conventional compounds, form interfering colored products with such constituents of urine as homogentisic acid and 5-hydroxyindole-3-acetic acid. The latter is a normal constituent of urine and as little as 1 mg% of such constituent in urine causes false positive results using the diazonium compounds described in this patent.

Another attempt to increase the sensitivity of the test strip-incorporated diazonium reagents is described in U.S. Pat. No. 3,853,476 which discloses the use of certain phosphoric acid diesters as sensitizing or potentiating agents for the reaction between the diazonium compound and bilirubin. However, due to the incompatibility between the phosphoric acid diesters and aqueous media, test strips prepared according to this patent must be manufactured by a double-impregnation process.

It should be mentioned that various so-called "accelerating agents" have been described in the art relative to the detection of bilirubin in serum by the diazo-coupling reaction. Such agents have included caffeine, dyphylline, sodium acetate, sodium benzoate, gum arabic, and various other chemically unrelated compounds.

The use of such accelerating agents in serum bilirubin tests was described in the literature as early as the 1920's but has never been applied in general to urinary bilirubin tests. This has been due to the generally recognized fact that such accelerating agents act on a form of bilirubin that is not present in significant amounts in urine. Such accelerators are reported to promote the diazo-coupling of free bilirubin.

However, no effect on the coupling of conjugated bilirubin has been reported, since in serum bilirubin tests the conjugated forms of bilirubin react relatively rapidly with the diazonium compounds without the need for accelerators. Hence, the conjugated forms of bilirubin in serum are referred to as direct-reacting bilirubin, whereas free bilirubin, which requires the presence of an accelerator in order to react rapidly, is referred to as indirect-reacting bilirubin. The fact that the scientific community views the effect of the reported accelerating agents as being restricted to the diazo-coupling reaction of free bilirubin, and not applicable to the reaction with conjugated bilirubin, is well supported by the concurrence of the primary review publications considered authorative in the art. For example, reference may be made to Henry, R. J., *Clinical Chemistry, Principles and Technics,* Harper and Row (1964) pp. 577–583; With, T. K., *Bile Pigments,* Academic Press (1968) pp. 324–327; and the *Journal of American Medical Technologists,* volume 31 (1969) pp. 707–710.

A single investigator has reported the use of dyphylline in a urinary bilirubin determination—*Scandanavian Journal of Clinical Laboratory Investigation,* supplement 56 (1961). However, such use was specifically designed to accomplish the same effect as discussed in the literature relative to serum bilirubin tests, namely, to accelerate the diazo-coupling of free bilirubin which, as is known, could only be present in the urine tested in very small amounts. The described procedure involves a cumbersome liquid test system, and there is no suggestion of a rapid and sensitive test strip system. Moreover, the described procedure has received little attention from those skilled in the art in their development of more sensitive bilirubin test strips, as is evidenced by their resort to the disadvantageous test systems disclosed in the previously discussed U.S. Pat. Nos. 3,853,476 and 3,880,588.

The present invention relates to a way of assessing both the reliability of the bilirubin-sensitive procedure selected, as well as the proficiency of the technician in assessing the results. This is achieved through the use of a reference or control sample—a test sample in which the chemical composition and physical characteristics simulate the test samples to be analyzed.

Exemplary of a commercially available control is CHEK-STIX®, marketed by Ames Division, Miles Laboratories, Inc., which utilizes unconjugated bilirubin present in a paper pad at the end of a plastic strip. When the strip is immersed in a predetermined volume of water for a predetermined time, a control solution results having a calibrated bilirubin concentration. The bilirubin used for this purpose is in the unconjugated form, and thus does not produce the same color as a pathological specimen containing bilirubin glucuronate conjugate. The present invention concerns itself with solving this problem. Thus, it provides a control solution, using unconjugated bilirubin, yet which does not provide atypical results in reagent systems devised to respond to pathological urine specimens containing bilirubin.

SUMMARY OF THE INVENTION

Briefly stated, the present invention comprises a composition for preparing a control solution for bilirubin analysis, a test device incorporating said composition, and methods for using both. The composition comprises a predetermined quantity of unconjugated bilirubin, and a mixture of each of a red, blue and yellow dye. The device comprises a carrier vehicle incorporated with the composition. The control solution is prepared by immersing the device in a predetermined quantity of water for a predetermined time, after which the device may be removed.

DETAILED DESCRIPTION OF THE INVENTION

As used herein, the term "carrier vehicle" is intended to include any means suitable for transporting a specified amount of the presently disclosed composition. It includes a capsule, such as a gelatin capsule, capable of dissolving in water or otherwise openable to release its contents. It can comprise a perforated capsule such that solvent can enter the capsule when used, and leach out the composition contained inside. It can also comprise foil or other material made into a sealed, easily openable package, the composition being sealed inside until eventual use, whereupon the package is opened and its contents emptied into a predetermined volume of water. Moreover, the carrier vehicle can comprise one or more carrier matrices, comprising a wide range of materials affixed to a support member. The carrier matrix is incorporated with the composition and, when used, is immersed in a predetermined volume of water for a predetermined time, and removed, leaving at least some of the composition behind in solution. Thus, the carrier vehicle can comprise a single carrier matrix incorporated with unconjugated bilirubin and the dyes as described herein. In another embodiment, the vehicle comprises two matrices attached to a support member, one matrix incorporated with the unconjugated bilirubin, the other with the dyes.

When a carrier matrix is utilized it can comprise any substance capable of being incorporated with the composition. Thus the matrix can take on many known forms such as those utilized for reagent strips for solution analysis. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the paper with part of a reagent system and impregnating the meshwork with other potentially incompatible reagents. French Pat. No. 2,170,397 teaches the use of carrier matrices having greater than 50% polyamide fibers therein. Another approach to carrier matrices is disclosed in U.S. Pat. No. 4,046,513 wherein the concept of printing reagents onto a suitable carrier matrix is employed. U.S. Pat. No. 4,046,514 discloses the interweaving or knitting of filaments bearing reagents in a reactant system. Preferably the carrier matrix comprises a bibulous material such as filter paper. All such carrier matrix concepts can be employed in the present invention, as can others, and all of the above-mentioned references describing same are hereby incorporated by reference into the present disclosure.

The base support member of the present test device may take on many variations in shape, size and material of construction. Thus, it might be constructed of any substantially liquid impervious material, such as polystyrene, polyolefin, glass, paper, metal or other material. Usually, however, it is preferred that the base member be of a polymeric material, such as biaxially oriented polystyrene sold by Plastic Suppliers, Inc. For most purposes it has been found preferable that the support member be relatively rigid and extend sufficiently far from the carrier matrix position to afford the user a convenient handle.

The composition of the present invention is normally solid at temperatures up to room temperature and higher. Moreover, it is sufficiently stable to enable storing for relatively long periods of time. It should be soluble in the system to be ultimately analyzed, such as an aqueous system. Finally, the dyes forming part of the composition must be capable of enabling a detectable response with the particular analysis procedure contemplated, such that the response to the control solution closely approximates that of a known concentration of conjugated bilirubin, e.g., bilirubin glucuronate.

The amount of bilirubin included in the device of the present invention, indeed the amount of composition imparted to the control solution, is dictated by the intended use of the ultimately formed control. Thus, if the particular bilirubin test system to be monitored is responsive to a very high range of bilirubin concentrations, more bilirubin would be required than where a more sensitive system were to be observed. Moreover, the amount of bilirubin also depends on the volume of control solution, larger volumes requiring more bilirubin than smaller. In a preferred embodiment of the invention, i.e. a device comprising two 1 by 1 cm pieces of filter paper mounted on a 1 by 8 cm strip of polystyrene film, only one of the paper pads contains bilirubin, and its amount ranges from about 0.01 to about 100 mg per pad. Preferably, the pad contains 0.1 to 1.5 mg of bilirubin.

In addition to unconjugated bilirubin, three types of dyes are included in the present invention as essential ingredients. These are representative of the colors red, blue and yellow. It is the presence of these dyes which enables the successful use of unconjugated bilirubin in the present invention. Bilirubin test instruments (which include the test strips described supra, as well as observational and spectrophotometrical procedures and related hardware), all rely on colorimetric phenomena. Thus, a test strip takes on a certain range of colors in the presence of pathological specimens of bilirubin glucuronate, the eye sees a particular color range, as do some spectrophotometric devices known in the art. However, in the presence of unconjugated bilirubin, the color ranges of all of these analytical techniques are changed; unconjugated bilirubin produces colors and colorimetric responses different from the conjugated form as it occurs in pathological specimens.

It has been found that this long-recognized, but unsolved, problem of obtaining a pure bilirubin-containing control solution can be virtually eliminated by providing a composition, or device incorporated with the composition, comprising unconjugated bilirubin and the abovementioned dyes. The amount of each dye required depends, as one might imagine, on the particular bilirubin-sensitive system to be ultimately used for the analysis, but given the benefit of the present disclosure, it is a routine laboratory procedure to adapt the invention to practically any system where a color range discrepancy exists between the system's response to the two forms of bilirubin.

In a preferred embodiment of the present invention, wherein the ultimate control solution is intended for use with dip-and-read reagent strips, the optimum amounts of dyes are present in a weight ratio of about 0.08–0.04 to 0.03–0.009 to 1 in the order of red, blue and yellow, respectively. Especially preferred for use with the bilirubin test area of N-MULTISTIX reagent strips is a weight ratio of about 0.06 to 0.01 to 1 in the order of red, blue and yellow dyes, respectively.

Many different dyes can be used, and their selection is both dependent on the ultimate analytical system to be employed, and easily within the ken of a skilled artisan, once he has been given the benefit of the present disclosure. Typical of red dyes suitable for use are FD&C red #40, #2 and #3, and D&C red #5, #6, #26, #28 and #33. Blue dyes which are acceptable include FD&C blue #1 and #2, and D&C blue #4 and #7. External D&C yellow #7, D&C yellow #10 and FD&C yellow #6 are among the yellow dyes useful herein. Especially suitable is the combination of FD&C red #40, FD&C blue #1 and External D&C yellow #7.

The preparation of the device of the present invention is reasonably straightforward, many of its aspects falling within well-known techniques of the art. Thus filter paper is impregnated with solutions of the ingredients, (bilirubin, the three dyes and other ancillary ingredients if desired), dried and mounted on a suitable support member, such as a polystyrene film, using a suitable adhesive. The resulting laminate is then cut to the desired size. Usually, the ingredient-bearing filter paper is mounted along one edge of a substantially wider plastic film. Thus, after slicing along the width dimension of the laminate, strips result having an impregnated pad portion at one end, the other serving as a handle.

In addition to the primary ingredients of bilirubin and the dyes, it may be desirable to include such ancillary ingredients as sodium carbonate, albumin and/or others in the impregnating solutions. For example, where two reagent areas are employed, one containing bilirubin, the other the dyes, it may be desirable to incorporate albumin in the bilirubin-containing solution. The reasons for this are two-fold: firstly, it may be desirable that the ultimate control solution contain albumin as well as bilirubin, and secondly, protein molecules such as albumin constitute excellent stabilizers for unconjugated bilirubin where long storage periods or relatively high temperature storage conditions are anticipated. Accordingly, the present invention comprises albumin in a preferred embodiment.

It has also been found desirable to incorporate an alkaline salt such as sodium carbonate with the dyes of the present invention where two reagent areas are utilized. Thus, in addition to the three dyes embraced by the present invention, such alkaline additives are within the scope thereof. Additional ancillary ingredients might include wetting agents, surfactants, and excipients.

While there are many adhesive means which would suffice for mounting the carrier matrix (or matrices) to the support material, all must satisfy the criteria of being substantially water insoluble, and contain no ingredients which would chemically contaminate the bilirubin and dye constituents or which would interfere with the response of the particular analytical system. It has been found that a double-faced adhesive tape, such as that commercially available as Double Stick Type 415 (3M Company), is especially adaptable to forming the device of the present invention.

EXAMPLES

The following Examples are provided to further shed light upon the preferred embodiments of the invention presently disclosed and claimed. As such, they are intended as being merely illustrative, and are not to be construed as limiting the scope of the claims appended hereto.

EXAMPLE I—Control Capsules

A device for preparing a control solution simulating human urine containing a pathological concentration of conjugated bilirubin is prepared. It comprises the composition of the present invention and, as a carrier vehicle, a Type 415 opaque gelatin capsule obtainable from Eli Lilly and Company. The composition comprises unconjugated bilirubin, FD&C red #40, FD&C blue #1 and External D&C yellow #7. The composition is formulated in accordance with the following recipe:

0.3 milligrams (mg) unconjugated bilirubin (Pfaanstiehl Laboratories, Inc.)
20.3 mg sodium carbonate (BASF Corp. Paramus, New Jersey)
3.0 mg External D&C yellow #7 (Pylon Products Co., Inc., New York, New York)
0.1 mg FD&C red #40 (Warner-Jenkinson Co., St. Louis, Missouri)
0.1 mg FD&C blue #1 (H. Kohnstamm, Inc., New York, New York)

The capsules are filled using a number 8 capsule filling machine obtainable from Parke, Davis & Company. The resultant capsules each contain 23.8 mg. of the composition.

EXAMPLE II—Preparation of a Bilirubin Control Solution and Its Use with N-MULTISTIX ®

A control capsule prepared as in Example I is used to prepare a bilirubin control solution responsive to the bilirubin test area of an N-MULTISTIX ® reagent strip marketed by the Ames Division of Miles Laboratories, Inc.

The contents of one capsule are added to 12 ml. distilled water and thoroughly mixed. An N-MULTISTIX reagent strip is momentarily immersed in the solution and the bilirubin-responsive reagent area observed for a color response. A positive response for bilirubin is indicated by the appearance of a purple color, which, when compared to the color chart on the bottle, is seen to be that expected from a urine containing the same amount of bilirubin as the control.

EXAMPLE III—Control Capsule

A device somewhat similar to that of Example I is prepared for use with a CLINI-TEK ® reflectance photometer, marketed by the Ames Division of Miles Laboratories, Inc. Accordingly, clear gelatin capsules are filled with the various ingredients listed below.

| Ingredient | Grams/1000 capsules |
|---|---|
| sodium carbonate | 20.3 |
| External D&C yellow #7 | 3.0 |
| FD&C red #40 | 0.1 |
| FD&C blue #1 | 0.1 |
| Bilirubin | 0.3 |

The ingredients are then used, after blending in a V-Blender, to fill bilirubin control capsules. One thousand clear gelatin capsules, size No. 0, obtainable from Eli Lilly and Company are uniformly charged with the ingredients using a number 8 capsule filling machine obtained from Parke, Davis and Company. The resultant capsules each contain 23.8 milligrams of the composition.

EXAMPLE IV—Preparation of a Bilirubin Control Solution and its Use with CLINI-TEK ® Reflectance Photometer A control capsule prepared as in Example III is used to prepare a bilirubin control solution responsive to the bilirubin test area of CLINI-TEK TM reagent strips, which strips are designed for use in conjunction with a CLINI-TEK ® reflectance photometer. The bilirubin test portion of the CLINI-TEK reagent strips utilizes chemistry similar to that of the bilirubin test portion of N-MULTISTIX reagent strips.

The contents of one capsule are added to 12 milliliters of distilled water and thoroughly mixed. A CLINI-TEK reagent strip is immersed in the solution and removed, and the wet strip inserted in the CLINI-TEK ® reflectance photometer. The instrument gives a reading of about +2 for bilirubin, indicating proper instrument response. Should the instrument read other than the predetermined response, it can be adjusted accordingly.

EXAMPLE V—Immersible Strip Bilirubin Control Device

A device for the preparation of a control solution simulating human urine containing a pathological concentration of bilirubin was prepared. A strip of filter paper (Schleicher & Schuell No. 470) was immersed in a solution prepared from the following ingredients, which were added in the order as listed, with stirring:

100 milliliters distilled water
1 gram External D&C yellow #7
5 grams sodium carbonate
65 milligrams FD&C red #40
13 milligrams FD&C blue #1

The dipped filter paper was dried at about 180° F. for about 15 minutes.

A second strip of filter paper (Schleicher & Schuell No. 470) was immersed in a solution prepared by combining the following ingredients in the order listed:

100 ml. distilled water
0.4 g NaOH 2.5 g bovine albumin (Pentex Division of Miles Laboratories, Inc.)

1.0 g unconjugated bilirubin (Pfaanstiehl Laboratories, Inc.)

The dipped filter paper was dried at about 180° F. for about 15 minutes.

The resultant impregnated dried papers were cut into squares measuring about 1 centimeter on a side. One of each of the two types of squares was mounted near one end of a strip of biaxially oriented polystyrene film (Plastic Suppliers, Inc.) measuring about 1 by 8 centimeters, using double-faced adhesive tape (Double Stick Type 415 from 3M Company) to provide a bilirubin control device.

EXAMPLE VI—Preparation of a Bilirubin Control Solution and Use with N-MULTISTIX ® Reagent Strips A device from Example V was immersed in 12 milliliters of distilled water for about 30 minutes and then removed, thus preparing a control solution simulating a urine containing a pathological amount of bilirubin.

The control solution thus prepared was then tested with the bilirubin-sensitive reagent area of an N-MULTISTIX reagent strip. A purple color developed in the bilirubin area indicative of a moderate elevation of bilirubin in urine.

What is claimed is:

1. A device useful in the preparation of a bilirubin control solution, said device comprising a carrier vehicle incorporated with a predetermined quantity of unconjugated bilirubin and a mixture of red, blue and yellow dyes.

2. The device of claim 1 wherein said dyes are present in a weight ratio of about 0.08–0.04 to 0.03–0.009 to 1, respectively.

3. The device of claims 1 or 2 wherein said dyes are FD&C red #40, FD&C blue #1 and External D&C yellow #7.

4. The device of claim 3 wherein said weight ratio is about 0.06 to 0.01 to 1.

5. A device useful in the preparation of a bilirubin control solution, said device comprising a support member having attached thereto a first carrier matrix incorporated with a predetermined quantity of unconjugated bilirubin, and a second carrier matrix incorporated with a mixture of red, blue and yellow dyes.

6. The device of claim 5 wherein said dyes are present in a weight ratio of about 0.08–0.04 to 0.03–0.009 to 1, respectively.

7. The device of claims 5 or 6 wherein said dyes are FD&C red #40, FD&C blue #1, and External D&C yellow #7.

8. The device of claim 7 wherein said weight ratio is about 0.06 to 0.01 to 1.

9. A composition useful in the preparation of a bilirubin control solution, said composition comprising a predetermined quantity of unconjugated bilirubin and a mixture of red, blue and yellow dyes.

10. The composition of claim 9 wherein said dyes are present in a weight ratio of about 0.08–0.04 to 0.03–0.009 to 1, respectively.

11. The composition of claims 9 or 10 wherein said dyes are FD&C red #40, FD&C blue #1, and External D&C yellow #7.

12. The composition of claim 11 wherein the weight ratio is about 0.06 to 0.01 to 1.

13. A method for preparing a bilirubin control solution comprising immersing the device of claims 1 or 2 in a predetermined volume of water.

14. A method for preparing a bilirubin control solution, comprising immersing the device of claim 3 in a predetermined volume of water.

15. A method for preparing a bilirubin control solution, comprising immersing the device of claim 4 in a predetermined volume of water.

16. A method for preparing a bilirubin control solution, comprising the consecutive steps of immersing the device of claim 5 or 6 in a predetermined volume of water for a predetermined time, and removing said device.

17. A method for preparing a bilirubin control solution, comprising the consecutive steps of immersing the device of claim 7 in a predetermined volume of water for a predetermined time, and removing said device.

18. A method for preparing a bilirubin control solution, comprising the consecutive steps of immersing the device of claim 8 in a predetermined volume of water for a predetermined time, and removing said device.

19. A method for determining the accuracy of a bilirubin test instrument, said method comprising the consecutive steps of:
   (a) forming a bilirubin control solution with the device of claim 1, 2, 5 or 6;
   (b) examining said solution with a test instrument capable of producing a predetermined detectable response to said control solution;
   (c) observing the actual response to the solution produced by said instrument; and
   (d) compensating for any discrepancy between said predetermined response and said actual response.

20. A method for determining the accuracy of a bilirubin test instrument, said method comprising the consecutive steps of:
   (a) forming a bilirubin control solution with the device of claim 3;
   (b) examining said solution with a test instrument capable of producing a predetermined detectable response to said control solution;
   (c) observing the actual response to the solution produced by said instrument; and
   (d) compensating for any discrepancy between said predetermined response and said actual response.

21. A method for determining the accuracy of a bilirubin test instrument, said method comprising the consecutive steps of:
   (a) forming a bilirubin control solution with the device of claim 4;
   (b) examining said solution with a test instrument capable of producing a predetermined detectable response to said control solution;
   (c) observing the actual response to the solution produced by said instrument; and
   (d) compensating for any discrepancy between said predetermined response and said actual response.

22. A method for determining the accuracy of a bilirubin test instrument, said method comprising the consecutive steps of:
   (a) forming a bilirubin control solution with the device of claim 7;
   (b) examining said solution with a test instrument capable of producing a predetermined detectable response to said control solution;
   (c) observing the actual response to the solution produced by said instrument; and (d) compensating for any discrepancy between said predetermined response and said actual response.

23. A method for determining the accuracy of a bilirubin test instrument, said method comprising the consecutive steps of:
 (a) forming a bilirubin control solution with the device of claim 8;
 (b) examining said solution with a test instrument capable of producing a predetermined detectable response to said control solution;
 (c) observing the actual response to the solution produced by said instrument; and
 (d) compensating for any discrepancy between said predetermined response and said actual response.

* * * * *